United States Patent [19]

Jonas et al.

[11] Patent Number: 4,916,128
[45] Date of Patent: Apr. 10, 1990

[54] THIADIAZINONES

[75] Inventors: Rochus Jonas, Darmstadt, Fed. Rep. of Germany; Jaime Piulats, Barcelona, Spain; Michael Klockow, Rossdorf, Fed. Rep. of Germany; Ingeborg Lues, Darmstadt, Fed. Rep. of Germany; Hans-Jochen Schliep, Traisa, Fed. Rep. of Germany

[73] Assignee: Merck Patent Gesellschaft mit Beschrankter Haftung, Darmstadt, Fed. Rep. of Germany

[21] Appl. No.: 202,294

[22] Filed: Jun. 6, 1988

[30] Foreign Application Priority Data

Jun. 6, 1987 [DE] Fed. Rep. of Germany ....... 3719031
Dec. 24, 1987 [DE] Fed. Rep. of Germany ....... 3744149

[51] Int. Cl.$^4$ .................. C07D 401/04; C07D 417/04; A61K 31/54
[52] U.S. Cl. .................. 514/213; 514/222.5; 514/183; 544/6; 544/8; 540/598; 540/523; 540/593
[58] Field of Search .............. 544/8, 6; 540/598, 523, 540/593; 514/213, 183, 222.5

[56] References Cited

U.S. PATENT DOCUMENTS 4,423,045 12/1983 Brown et al. ................. 514/222
4,678,785 7/1987 Ao et al. ..................... 514/222

OTHER PUBLICATIONS

Ao et al, Chemical Abstracts, vol. 105, entry 97488n (1986).

*Primary Examiner*—John M. Ford
*Attorney, Agent, or Firm*—Millen, White & Zelano

[57] ABSTRACT

Thiadiazinones of the formula I

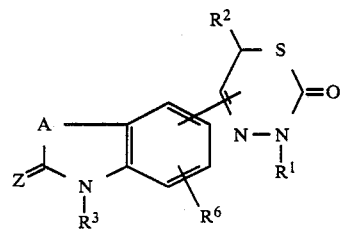

wherein

A is —CHR$^4$—CHR$^5$—, —CH$_2$—CR$^4$R$^5$—, —CR$^4$R$^5$—CH$_2$—, —CHR$^4$—CHR$^5$—CH$_2$—, —CHR$^4$—CH$_2$—CHR$^5$—, —CH$_2$—CHR$^4$—CHR$^5$—, —CR$^4$R$^5$—CH$_2$CH$_2$—, —CH$_2$—CR$^4$R$^5$—CH$_2$— or —CH$_2$CH$_2$—CR$^4$R$^5$—,

R$^1$, R$^2$, R$^3$, R$^4$ and R$^5$ are each independently H, C$_{1-5}$-alkyl, C$_{2-5}$-alkenyl or C$_{2-5}$-alkinyl, R$^3$ is also C$_{1-15}$-acyl, R$^6$ is H, alkyl, alkoxyl, OH, F, Cl, Br or I and Z is (H, H), (H, alkyl), (alkyl, alkyl) or O, the alkyl, alkenyl, alkinyl and/or alkoxy groups in each case containing up to 5 C atoms, but wherein, if A is —CH$_2$CH$_2$— and Z is O, one of the radicals R$^1$, R$^2$, R$^3$ and R$^6$ must be other than H, and salts thereof demonstrate positive inotropic action and are suitable for combating cardiovascular diseases.

18 Claims, No Drawings

THIADIAZINONES

BACKGROUND OF THE INVENTION

The invention relates to new thiadiazinones of the formula

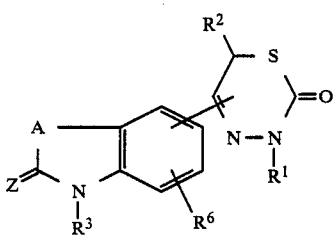

wherein

A is $-CHR^4-CHR^5-$, $-CH_2-CR^4R^5-$, $-CR^4R^5-CH_2-$, $-CHR^4-CHR^5-CH_2-$, $-CHR^4-CH_2-CHR^5-$, $-CH_2-CHR^4-CHR^5-$, $-CR^4R^5-CH_2CH_2-$, $-CH_2-CR^4R^5-CH_2-$ or $-CH_2CH_2-CR^4R^5-$, $R^1$, $R^2$, $R^3$, $R^4$ and $R^5$ are each H, alkyl, alkenyl or alkinyl, $R^3$ is also acyl with 1-15 C atoms, $R^6$ is H, alkyl, alkoxy, OH, F, Cl, Br or I and Z is (H, H), (H, alkyl), (alkyl, alkyl) or O, the alkyl, alkenyl, alkinyl and/or alkoxy groups in each case containing up to 5 C atoms, but wherein, if A is $-CH_2CH_2-$ and Z is O, one of the radicals $R^1$, $R^2$, $R^3$ and $R^6$ must be other than H, and salts thereof.

A compound corresponding to formula I but wherein A is $-CH_2-CH_2-$, Z is O and $R^1$, $R^2$, $R^3$ and $R^6$ are each H is known from EP-A-0,180,158.

SUMMARY OF THE INVENTION

It is an object of the invention to provide new compounds with useful properties, in particular those which can be used for the preparation of medicaments.

Upon further study of the specification and appended claims, further objects and advantages of this invention will become apparent to those skilled in the art.

These objects have been satisfied by the provision of compounds of the formula

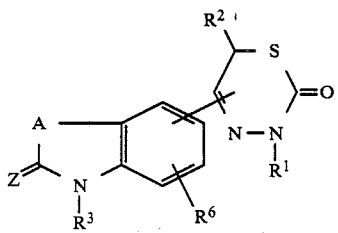

wherein

A is $-CHR^4-CHR^5-$, $-CH_2-CR^4R^5-$, $-CR^4R^5-CH_2-$, $-CHR^4-CHR^5-CH_2-$, $-CHR^4-CH_2-CHR^5-$, $-CH_2-CHR^4-CHR^5-$, $-CR^4R^5-CH_2CH_2-$, $-CH_2-CR^4R^5-CH_2-$ or $-CH_2CH_2-CR^4R^5-$, $R^1$, $R^2$, $R^3$, $R^4$ and $R^5$ are each independently H, $C_{1-5}$-alkyl, $C_{2-5}$-alkenyl or $C_{2-5}$-alkinyl, $R^3$ is also $C_{1-15}$-acyl, $R^6$ is H, $C_{1-5}$-alkyl, $C_{1-5}$-alkoxy, OH, F, Cl, Br or I and Z is 2 hydrogen atoms, H and $C_{1-5}$-alkyl, 2 independent $C_{1-5}$-alkyl groups or an oxygen atom and salts thereof, wherein, if A is $-CH_2CH_2-$ and Z is O, at least one of $R^1$, $R^2$, $R^3$ or $R^6$ is not H.

DETAILED DISCUSSION

It has been found that the compounds of formula I have useful pharmacological properties, coupled with good tolerability. In particular, they exhibit an action on the force of the heart (positive inotropic activity); the substances furthermore have a vasodilating action and therefore promote circulation. The vasodilating action and the cardiac action can be determined, for example, on anaesthetized or conscious dogs, cats, monkeys or minipigs, and the positively inotropic action can also be determined on isolated heart preparations (for example atrium, papillary muscle or perfused whole heart) from rats, guineapigs, cats or dogs, for example in accordance with methods such as are described in Arzneimittelforschung, Volume 31 (I) No. 1a (1981), pages 141 to 170, or by Schliep et al. in 9th International Congress of Pharmacol., London, Abstracts of papers 9P.

Antithrombotic and platelet aggregation-inhibiting properties and properties which influence the shape of erythrocytes furthermore arise. The influencing of platelet function in the sense of inhibition of aggregation can be demonstrated on rats ex vivo in the test in accordance with the method of Born (Nature 194, 927–929, 1962). The anti-thrombotic action manifests itself in the increase in bleeding time in accordance with the method of Stella (Thrombos. Res. 7, 709–716, 1975), in the reduction in the thrombus weight on thrombozing of the jugular vein induced by low temperatures in rats in accordance with the method of Meng (Ther. Ber. 47, 69–79, 1975) and in the increase of the laser pulse required for complete thrombozing in the mesenteric venules of rats in accordance with a modification of the method of Kovacs (Micro-vasc. Res. 6, 194–201, 1973).

The favorable action on erythrocyte deformability can be detected in a nucleopore filter by the method of Schmid-Schönbein (Pflüger's Archiv 338, 93–114, 1973). Favorable effects on the fibrinolysis/euglobulinolysis time can also be detected in accordance with the method of v. Kaulla (Progr. Chem. Fibrinol, Thrombol. 1, 131–149, 1975; ed. J. F. Davidson, Raven Press, N.Y.).

The compounds can therefore be used as medicament active compounds in human and veterinary medicine. They can furthermore be used as intermediate products for the preparation of other medicament active compounds.

The invention accordingly relates to compounds of the formula I and a process for their preparation, characterized in that a ketone of the formula II

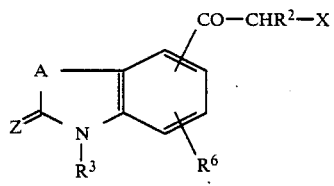

wherein

X is Cl, Br, I or a reactively esterified OH group and A, $R^2$, $R^3$, $R^6$ and Z have the meanings given, is reacted with a compound of the formula III $$H_2N\text{-}NR^1\text{-}CS\text{-}OR \qquad \qquad III$$

wherein

R is alkyl with 1–5 C atoms or one equivalent of a metal or ammonium cation and $R^1$ has the meaning given, and/or in that, if appropriate, a compound of the formula I wherein $R^1$ and/or $R^3$ is H is treated with an alkylating, alkenylating, alkinylating or acylating agent and/or a base of the formula I is converted into one of its salts by treatment with an acid.

Above and below A, $R^1$ to $R^6$, Z, X and R have the meanings given in the case of formulae I, II and III, unless expressly indicated otherwise.

In the formulae, alkyl is preferably unbranched, preferably has 1, 2 or 3 C atoms, and is preferably methyl, and furthermore preferably ethyl or propyl, or moreover preferably isopropyl, butyl, isobutyl, sec.-butyl, tert.-butyl, n-pentyl or isopentyl. Alkenyl is preferably unbranched, preferably has 2 or 3 C atoms and is preferably allyl, or furthermore preferably vinyl or propen-1-yl. Alkinyl is preferably unbranched, preferably has 2 or 3 C atoms and is preferably propargyl, or furthermore preferably ethinyl or propin-1-yl.

Acyl is the acid radical of a carboxylic or sulfonic acid, preferably alkanoyl, alkenoyl or alkinoyl with 1–10, in particular 1,2,3,4 or 5 C atoms, and specifically preferably acetyl, or furthermore preferably formyl, propionyl, butyryl, isobutyryl, valeryl, isovaleryl or pivaloyl (trimethylacetyl), acryloyl, hydroxyacetyl, methoxyacetyl, chloroacetyl, aminoacetyl(glycyl), N-methylaminoacetyl, N,N-dimethylaminoacetyl, N,N-diethylaminoacetyl, pyrrolidinoacetyl, piperidinoacetyl; or moreover preferably optionally substituted aroyl with 7–15 C atoms, possible substituents being, in particular, 1–3, preferably one, of the following groups: alkyl, alkoxy, alkylthio, alkylsulfinyl or alkylsulfonyl with in each case 1–3, preferably 1 or 2 C atoms, methylenedioxy, or furthermore OH, F, Cl, Br, I, $NO_2$, $NH_2$ or alkylamino or dialkylamino with in each case 1–3, preferably 1 or 2 C atoms in the alkyl group. Individual preferred aroyl radicals are benzoyl, o-, m- or p-toluyl, o-, m- or p-methoxybenzoyl, 2,3-, 2,4-, 2,5-, 2,6-, 3,4- or 3,5-dimethoxybenzoyl, 2,3,4-, 2,3,5-, 2,3,6-, 2,4,5-, 2,4,6- or 3,4,5-trimethoxybenzoyl, o-, m- or p-methylthiobenzoyl, o-, m- or p-methylsulfinylbenzoyl, o-, m- or p-methylsulfonylbenzoyl, 2,3- or 3,4-methylenedioxybenzoyl, o-, m- or p-fluorobenzoyl, o-, m- or p-chlorobenzoyl, 2- or 3-methoxy-4-methylthiobenzoyl, 2- or 3-methoxy-4-methylsulfinylbenzoyl, o-, m- or p-dimethylaminobenzoyl, 2- or 3-methoxy-4-(2-hydroxyethoxy)-benzoyl, 2- or 3-methoxy-4-(2-methoxyethoxy)-benzoyl, or 1- or 2-naphthoyl. Acyl can furthermore be heterocyclocarbonyl with 2–10 C atoms, such as 2- or 3-furoyl, 2- or 3-thenoyl, isoxazolyl-4-carbonyl, 3-phenyl-5-methyl-isoxazolyl-4-carbonyl, 1,5-dimethylpyrazolyl-3-carbonyl, 2-methyl-thiazolyl-4- or -5-carbonyl, 1-imidazolyl-carbonyl, picolinoyl, nicotinoyl, isonicotinoyl, 1-methyl-2-, -3- or -4-piperidinylcarbonyl, or furthermore, $C_{6-10}$-aryl-$C_{1-4}$-alkanoyl, such as phenylacetyl, o-, m- or p-methoxyphenylacetyl, 2- or 3-phenylpropionyl, 2-, 3- or 4-phenylbutyryl; or $C_{3-8}$-cycloalkylcarbonyl, such as cyclopropylcarbonyl, cyclopentylcarbonyl, cyclohexylcarbonyl; or $C_{1-8}$-alkylsulfonyl, such as methyl-, ethyl-, propyl- or butylsulfonyl; or $C_{6-15}$-arylsulfonyl, such as benzenesulfonyl, o-, m- or p-toluenesulfonyl, o-, m- or p-methoxybenzenesulfonyl, 1- or 2-naphthalenesulfonyl.

Additional acyl groups which are particularly preferred are derived from carbonic acid and its esters and also from carbamic acid and its N-$C_{1-8}$-alkyl-, N,N-di-$C_{1-8}$-alkyl-, N-$C_{6-15}$-aryl- and N-$C_{1-8}$-alkanoyl derivatives. Preferable example of such acyl groups are: alkoxycarbonyl such as methoxycarbonyl, ethoxycarbonyl, propoxycarbonyl, isopropoxycarbonyl, butoxycarbonyl or isobutoxycarbonyl; fluorinated $C_{1-8}$-alkoxycarbonyl such as 2,2,2-trifluoroethoxycarbonyl; cycloalkoxycarbonyl such as cyclopropoxycarbonyl, cyclobutoxycarbonyl, cyclopentoxycarbonyl or cyclohexoxycarbonyl; $C_{6-10}$-aryloxycarbonyl such as phenoxycarbonyl, o-, m- or p-methoxyphenoxycarbonyl; aminocarbonyl; N-$C_{1-8}$-alkylaminocarbonyl such as N-methyl- or N-ethylaminocarbonyl; N,N-di-$C_{1-8}$-alkylaminocarbonyl such as N,N-dimethyl- or N,N-diethylaminocarbonyl; N-$C_{3-8}$-cycloalkylaminocarbonyl such as N-cyclopropylaminocarbonyl, N-cyclobutylaminocarbonyl, N-cyclopentylaminocarbonyl, N-cyclohexylaminocarbonyl, N,N-di-$C_{3-8}$-cycloalkylaminocarbonyl such as N,N-dicyclopropylaminocarbonyl; pyrrolidinocarbonyl; piperidinocarbonyl; N-$C_{6-10}$-arylaminocarbonyl such as anilinocarbonyl; $C_{1-8}$-alkanoylaminocarbonyl such as formylaminocarbonyl, acetylaminocarbonyl, propionylaminocarbonyl, butyrylaminocarbonyl, isobutyrylaminocarbonyl.

Alkoxy is preferably unbranched, preferably has 1, 2 or 3 C atoms and is preferably methoxy, or furthermore preferably ethoxy or propoxy, or moreover, for example, isopropoxy, butoxy, isobutoxy, sec.-butoxy, tert.-butoxy, pentoxy or isopentoxy.

The dihydrothiadiazinone ring is preferably in the 6-position, or furthermore preferably in the 7-position of the tetrahydroquinoline ring and preferably in the 7-position, or furthermore preferably in the 8-position of the tetrahydrobenzazepine ring; however, it can also be in the 5- or 8-position of the tetrahydroquinoline ring or in the 6- or 9-position of the tetrahydrobenzazepine ring.

The radicals $R^1$, $R^2$, $R^3$, $R^4$, $R^5$ and $R^6$ are preferably each H or methyl. Specifically, they have the following preferred meanings: $R^1$ is H or methyl, $R^2$ is methyl; $R^3$ is H or methyl, or furthermore also formyl, acetyl or propionyl; $R^4$ is H or methyl; $R^5$ is H or methyl; and $R^6$ is H. A is preferably —$CH_2$—$CR^4R^5$—, in particular —$CH_2CH_2$— or —$CH_2$—$C(CH_3)_2$—, or —$CH_2CH_2$—$CR^4R^5$—, in particular —$CH_2CH_2CH_2$— or —$CH_2CH_2C(CH_3)_2$—.

The radical Z is preferably (H, H), especially if the radical $R^3$ at the same time is acyl, or O, especially if at the same time the radical $R^3$ is H, alkyl, alkenyl or alkinyl.

The invention particularly relates to tetrahydroquinolinyl-1,3,4-thiadiazin-2-one derivatives of formula I, wherein A is $CHR^4$—$CHR^5$—, —$CH_2$—$CR^4R^5$— or —$CR^4R^5$—$CH_2$— ("formula Ia") and to tetrahydrobenzazepinyl-1,3,4-thiadiazin-2-one derivatives of formula I wherein A is —$CHR^4$—$CHR^5$—$CH_2$—, —$CHR^4$—$CH_2$—$CHR^5$—, —$CH_2$—$CHR^4$—$CHR^5$—, —$CR^4R^5$—$CH_2CH_2$—, —$CH_2$—$CR^4R^5$—$CH_2$— or —$CH_2CH_2$—$CR^4R^5$— ("formula Ib"). Preferred are those compounds of formulae I, Ia and Ib in which at least one of the radicals mentioned has one of the above-mentioned preferred meanings. Some preferred groups of compounds of the formulae Ia or Ib, respectively, can be expressed by the following part-formulae Iaa to Iad or Iba to Ibd, respectively, which correspond to the formulae Ia or Ib, respectively and wherein the radicals which are not described in more detail have the meaning given in the case of formulae I, Ia or Ib, respectively, but wherein in Iaa the dihydrothiadiazinone ring is in the 6-position.
$R^1$ is H,
$R^2$, $R^3$, $R^4$ and $R^5$ are each H or methyl,
$R^6$ is H and
Z is O;
in Iab, the dihydrothiadiazinone ring is in the 6- or 7-position,
$R^1$ is H or alkyl with 1–3 C atoms,
$R^2$, $R^4$ and $R^5$ are each H or methyl,
$R^3$ is acyl with 1–10 C atoms,
$R^6$ is H and
Z is (H,H);
in Iac, the dihydrothiadiazinone ring is in the 6- or 7-position,
$R^1$ is H or alkyl with 1–3 C atoms,
$R^2$, $R^4$ and $R^5$ are each H or methyl,
$R^3$ is alkanoyl with 1–6 C atoms, benzoyl, toluyl, methoxybenzoyl, dimethoxybenzoyl, methylthiobenzoyl, methylsulfinyl-benzoyl, methylsulfonylbenzoyl, picolinoyl, nicotinoyl, isonicotinoyl, alkylsulfonyl with 1–6 C atoms, benzenesulfonyl or toluenesulfonyl,
$R^6$ is H and
Z is (H,H);
in Iad, the dihydrothiadiazinone ring is in the 6- or 7-position,
$R^1$ is H or alkyl with 1–3 C atoms,
$R^2$, $R^4$ and $R^5$ are each H or methyl,
$R^3$ is alkanoyl with 1–5 C atoms,
$R^6$ is H and
Z is (H,H);
in Iba the dihydrothiadiazinone ring is in the 7-position,
$R^1$ is H,
$R^2$, $R^3$, $R^4$ and $R^5$ are each H or methyl,
$R^6$ is H and
Z is O;
in Ibb the dihydrothiadiazinone ring is in 7- or 8-position,
$R^1$ is H or alkyl with 1–3 C atoms,
$R^2$, $R^4$ and $R^5$ are each H or methyl,
$R^3$ is acyl with 1–10 C atoms,
$R^6$ is H and
Z is (H,H);
in Ibc the dihydrothiadiazinone ring is in 7- or 8-position,
$R^1$ is H or alkyl with 1–3 C atoms,
$R^2$, $R^4$ and $R^5$ are each H or methyl,
$R^3$ is alkanoyl with 1–6 C atoms, dialkylaminoalkanoyl with 4–10 C atoms, cyclohexylcarbonyl, benzoyl, toluyl, methoxybenzoyl, dimethoxybenzoyl, methylthio-benzoyl, methylsulfinyl-benzoyl, methylsulfonyl-benzoyl, fluorobenzoyl, methoxymethylthiobenzoyl, 2- or 3-thenoyl, picolinoyl, nicotinoyl, isonicotinoyl, alkylsulfonyl with 1–6 C atoms, benzene sulfonyl, toluene sulfonyl, alkoxycarbonyl with 2–6 C atoms, phenoxycarbonyl, aminocarbonyl, alkylaminocarbonyl with 2–6 C atoms, dialkylaminocarbonyl with 3–9 C atoms or alkanoylaminocarbonyl with 2–6 C atoms,
$R^6$ is H and
Z is (H,H);
in Ibd the dihydrothiadiazinone ring is in 7-position,
$R^1$, $R^4$, $R^5$ and $R^6$ are each H,
$R^2$ is methyl,
$R^3$ is cyclohexylcarbonyl, methoxybenzoyl, dimethoxybenzoyl, fluorobenzoyl, 2-methoxy-4-methylthiobenzoyl, 2-thenoyl, isonicotinoyl, methoxycarbonyl, ethoxycarbonyl or phenoxycarbonyl and
Z is (H,H).

The compounds of the formula I are moreover prepared by methods which are known per se, such as are described in the literature (for example in the standard works, such as Houben-Weyl, Methoden der Organischen Chemie (Methods of Organic Chemistry), Georg-Thieme-Verlag, Stuttgart; in particular in European Pat. No. 0,180,158), and in particular under reaction conditions which are known and suitable for the reactions mentioned. In selecting these conditions it is possible to make use of variants which are known per se and are not mentioned in more detail here.

In the compounds of the formula II, X is preferably Cl or Br. If X is a reactively esterified OH group, this is preferably alkylsulfonyloxy with 1–6 C atoms, for example methanesulfonyloxy, or arylsulfonyloxy with 6–10 C atoms, for example benzene-, p-toluene- or 1- or 2-naphthalenesulfonyloxy.

In the compounds of the formula II, R is preferably methyl or ethyl, or also Na, K or $NH_4$.

If desired, the starting substances can also be formed in situ such that they are not isolated from the reaction mixture but are immediately reacted further to give the compounds of the formula I. On the other hand, it is possible to carry out the reaction in stages, in which case further intermediate products can be isolated.

The starting substances of the formulae II and III are known in some cases. Where they are not known, they can be prepared by methods which are known per se. The ketones of the formula II are accessible, for example, by Friedel-Crafts synthesis from corresponding tetrahydroquinoline or tetrahydrobenzazepine derivatives using compounds of the formula X—CO—CH-$R^2$—X.

Specifically, the reaction of the ketones of the formula II with the compounds of the formula III is carried out in the presence or absence of an inert solvent at temperatures between about −20° and about +150°, preferably between 20° to 100°. Examples of suitable solvents are hydrocarbons, such as benzene, toluene, xylenes or mesitylene; halogenated hydrocarbons, such as methylene chloride, trichloroethylene or chlorobenzene; alcohols, such as methanol, ethanol or isopropanol; glycols and glycol ethers, such as ethylene glycol, diethylene glycol and 2-methoxyethanol; nitriles, such as acetonitrile; ethers, such as tetrahydrofuran or dioxane; amides, such as dimethylformamide (DMF); and sulfoxides, such as dimethyl sulfoxide. Mixtures of these solvents are also suitable.

If desired, a compound of the formula I wherein $R^1$ and/or $R^3$ are H can be alkylated, alkenylated, alkinylated or acylated, the corresponding compounds of the formula I wherein $R^1$ and/or $R^3$ is alkyl, alkenyl or alkinyl or $R^3$ is also acyl being obtained.

Suitable alkylating, alkenylating, alkinylating or acylating agents are, for example, the corresponding chlorides, bromides or iodides of the formulae $R^1$-X or $R^3$-X (wherein $R^1$ and/or $R^3$ are other than H), and suitable acylating agents are also the anhydrides of the formula $(R^3)_2O$ ($R^3$=acyl). These reactions are advantageously carried out in the presence or absence of an inert solvent at temperatures between about −20° and about 200°, preferably between 0° and 150°. Suitable solvents are those mentioned above. The addition of a base in the reaction is advantageous. Suitable bases are, for example, alkali metal or alkaline earth metal hydroxides, carbonates, alcoholates or hydrides, such as sodium or potassium hydroxide, carbonate, methylate, ethylate or hydride, and furthermore, especially for the acylation, also secondary or tertiary amines, for example triethylamine or pyridine.

If a compound of the formula I wherein $R^1=R^3=H$ is alkylated, the radical $R^1=$alkyl is first introduced; compounds of the formula I where $R^1=$alkyl and $R^3=H$ and where $R^1=R^3=$alkyl are therefore readily obtainable by subsequent alkylation.

A base of the formula I can be converted with an acid into the associated acid addition salt. Possible acids for this reaction are, in particular, those which give physiologically acceptable salts. It is thus possible to use inorganic acids, for example sulfuric acid, nitric acid, hydrogen halide acids, such as hydrochloric acid or hydrobromic acid, phosphoric acids, such as orthophosphoric acid, or sulfamic acid, and furthermore organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, slaicyclic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids and laurylsulfuric acid. Salts with physiologically unacceptable acids, for example picrates, can be used to purify the compounds of the formula I.

Compounds of the formula I can contain one or more centers of asymmetry. In this case, they are usually present in racemic form. Racemates obtained can be resolved mechanically or chemically into their optical antipodes by methods which are known per se. Preferably, diastereomers are formed from the racemic mixture by reaction with an optically active resolving agent. Suitable resolving agents for basic compounds of the formula I are, for example, optically active acids, such as the D- and L-forms of tartaric acid, diacetyltartaric acid, dibenzoyltartaric acid, mandelic acid, malic acid and lactic acid, or the various optically active camphorsulfonic acids, such as $\beta$-camphorsulfonic acid.

It is of course also possible to obtain optically active compounds of the formula I by the methods described above by using starting substances which are already optically active.

The invention furthermore relates to the use of the compounds of the formula I and their physiologically acceptable salts for the preparation of pharmaceutical formulations, in particular by a non-chemical route. They can here be brought into a suitable dosage form together with at least one solid, liquid and/or semi-liquid excipient or auxiliary and if appropriate in combination with one or more further active compounds.

The invention furthermore relates to agents, in particular pharmaceutical formulations, containing at least one compound of the formula I and/or one of its physiologically acceptable salts.

These formulations can be used as medicaments in human and veterinary medicine. Possible excipients are organic or in-organic substances which are suitable for enteral (for example oral), parenteral or topical administration and do not react with the new compounds, for example water, vegetable oils, benzyl alcohols, polyethylene glycols, glycerol triacetate, gelatine, carbohydrates, such as lactose or starch, magnesium stearate, talc or petroleum jelly. Tablets, coated tablets, capsules, syrups, elixirs or drops are used, in particular, for oral administration, suppositories are used for rectal administration, solutions, preferably oily or aqueous solutions, and furthermore suspensions, emulsions or implants are used for parenteral administration and ointments, creams or powders are used for topical application. The new compounds can also be lyophilized and the resulting lyophilisates can be used, for example, for the production of injection preparations. The formulations mentioned can be sterilized and/or contain auxiliaries, such as lubricants, preservatives, stabilizers and/or wetting agents, emulsifiers, salts for influencing the osmotic pressure, buffer substances, colouring substances, flavouring substances and/or aroma substances. If desired, they can also contain one or more other active compounds, for example one or more vitamins.

The compounds of the formula I can be used in combating diseases, in particular cardiac insufficiency, and in the therapeutic treatment of the human or animal body.

The substances according to the invention are thereby as a rule administered analogously to known positively inotropic substances, such as amrinone, preferably in dosages of between about 1 and 100 mg, in particular between 2 and 20 mg per dosage unit. The daily dosage is preferably between about 0.02 and 2 mg/kg of body weight. However, the specific dose for each particular patient depends on the most diverse factors, for example on the activity of the specific compound used, on the age, body weight, general state of health, sex, on the diet, on the administration time and route and the rate of excretion, medicament combination and severity of the particular disease to which the therapy applies. Oral administration is preferred. In contrast to the Digitalis glycosides used to date for the therapy of cardiac insufficiency, the compounds of the formula I are distinguished by an improved therapeutic range and peripheral relief.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

In the following examples, "customary working up" means:

Water or dilute sodium hydroxide solution is added if necessary, the mixture is extracted with an organic solvent, such as ethyl acetate, chloroform or methylene chloride, the phases are separated, the organic phase is dried over sodium sulfate, filtered and evaporated and the residue is purified by chromatography and/or crystallization.

EXAMPLE 1

2.15 g of O-ethyl hydrazine-thioformate are added to a solution of 2.8 g of 6-(2-chloropropionyl)-2-oxo-1,2,3,4-tetrahydroquinoline (obtainable from 1,2,3,4-tetrahydro-2-oxo-quinoline and 2-chloropropionyl chloride by a Friedel-Crafts reaction) in 40 ml of acetonitrile and the mixture is boiled for 2 hours. The mixture is concentrated, the concentrate is cooled and the resulting 5-(2-oxo-1,2,3,4-tetrahydroquinolin-6-yl)-6-methyl-3,6-dihydro-1,3,4-thiadiazin-2-one ("A") is filtered off and recrystallized from methanol. Melting point 278°.

The following 3,6-dihydro-1,3,4-thiadiazin-2ones are obtained analogously:

5-(2-oxo-1,2,3,4-tetrahydroquinolin-6-yl)-3,6-dimethyl-, melting point 214°-216°
5-(2-oxo-1,2,3,4-tetrahydroquinolin-6-yl)-3-ethyl-6-methyl-, melting point 168°-169°
5-(1-methyl--2-oxo-1,2,3,4-tetrahydroquinolin-6-yl)-5-(1-methyl-2-oxo-1,2,3,4-tetrahydroquinolin-6-yl)-6-methyl-, melting point 215°-217°
5-(1-methyl-2-oxo-1,2,3,4-tetrahydroquinolin-6-yl)-3,6-dimethyl-, melting point 137°-139°
5-(2-oxo-4,4-dimethyl-1,2,3,4-tetrahydroquinolin-6-yl)-
5-(2-oxo-4,4-dimethyl-1,2,3,4-tetrahydroquinolin-6-yl)-6-methyl-, melting point 297°-297°
5-(2-oxo-4,4-dimethyl-1,2,3,4-tetrahydroquinolin-6-yl)-3,6-dimethyl-, melting point 243°-244°
5-(1,4,4-trimethyl-2-oxo-1,2,3,4-tetrahydroquinolin-6-yl)
5-(1,4,4-trimethyl-2-oxo-1,2,3,4-tetrahydroquinolin-6-yl)-6-methyl-, melting point 241°
5-(1,4,4-trimethyl-2-oxo-1,2,3,4-tetrahydroquinolin-6-yl)-3,6-dimethyl-
5-(1-ethyl-4,4-dimethyl-2-oxo-1,2,3,4-tetrahydroquinolin-6-yl)-6-methyl-
5-(1-isopropyl-4,4-dimethyl-2-oxo-1,2,3,4-tetrahydroquinolin-6-yl)-6-methyl-, melting point 193°
5-(1-acetyl-2-oxo-1,2,3,4-tetrahydroquinolin-6-yl)-
5-(1-acetyl-2-oxo-1,2,3,4-tetrahydroquinoline-6-yl)-6-methyl-
5-(1-acetyl-2-oxo-1,2,3,4-tetrahydroquinolin-6-yl)-3,6-dimethyl-
5-(1-acetyl-2-oxo-4,4-dimethyl-1,2,3,4-tetrahydroquinolin-6-yl)-
5-(1-acetyl-2-oxo-4,4-dimethyl-1,2,3,4-tetrahydroquinolin-6-yl)-6-methyl-and
5-(1-acetyl-2oxo-4,4-dimethyl-1,2,3,4-tetrahydroquinolin-6-yl)-3,6-dimethyl-.

EXAMPLE 2

5-(1,2,3,4-Tetrahydroquinolin-6-yl)-6-methyl-3,6-dihydro-1,3,4-thiadiazin-2-one ("B"), melting point 168°, is obtained analogously to Example 1 from 1,2,3,4-tetrahydro-6-(2-chloropropionyl)-quinoline [obtainable by reaction of 1-acetyl-1,2,3,4-tetrahydroquinline with 2-chloropropionyl chloride/AlCl$_3$ to give 1-acetyl-1,2,3,4-tetrahydro-6-(2-chloropropionly)-quinoline (and in addition the 7-(2-chloropropionyl) isomer, which can be removed chromatographically) and subsequent splitting off of the acetyl group with HCl].

5-(1,2,3,4-Tetrahydroquinolin-7-yl)-6-methyl-3,6-dihydro-1,3,4-thiadiazin-2-one is obtained analogously from 1,2,3,4-tetrahydro-7-(2-chloropropionyl)-quinoline.

EXAMPLE 3

5-(1-Acetyl-1,2,3,4-tetrahydroquinolin-6-yl)-6-methyl-3,6-dihydro-1,3,4-thiadiazin-2-one ("C"), melting point 207°, is obtained analogously to Example 1 from 1-acetyl-1,2,3,4-tetrahydro-6-(2-chloropropionyl)-quinoline.

The following compounds are obtained analogously from the corresponding tegrahydroquinolines: 5-(1-acetyl-1,2,3,4-tetrahydroquinolin-7-yl)-6-methyl-3,6-dihydro-1,3,4-thiadiazin-2-one, melting point 174° 5-(1-acetyl-4,4-dimethyl-1,2,3,4-tetrahydroquinolin-7-yl)-6-methyl-3,6-dihydro-1,3,4-thiadiazin-2-one, m.p. 166°.

EXAMPLE 4

0.32 g of NaH is added to a solution of 3 g of "A" in 40 ml of DMF, while cooling with ice, and the mixture is stirred for 1 hour. After addition of 1.5 ml of ethyl iodide, the mixture is stirred at 20° for 2 hours. The mixture is evaporated, water is added and the resulting 5-(2-oxo-1,2,3,4-tetrahydroquinolin-6-yl)-3-ethyl-6-methyl-3,6-dihydro-1,3,4-thiadiazin-2-one is filtered off; melting point 168°-169° (from isopropanol).

The following 3,6-dihydro-1,3,4-thiadiazin-2-ones are obtained analogously by alkylation, alkenylation or alkinylation of the corresponding compounds of the formula I ($R^1$=H):

5(2-oxo-1,2,3,4-tetrahydroquinolin-6-yl)-3-methyl-
5-(2-oxo-1,2,3,4-tetrahydroquinolin-6-yl)-3-ethyl-
5-(2-oxo-1,2,3,4-tetrahydroquinolin-6-yl)-3-butyl-
5-(2-oxo-1,2,3,4-tetrahydroquinolin-6-yl)-6-methyl-3-propyl-
5-(2-oxo-1,2,3,4-tetrahydroquinolin-6-yl)-3-isopropyl-6-methyl-, melting point 195°-196°
5-(2-oxo-1,2,3,4-tetrahydroquinolin-6-yl)-3-butyl-6-methyl-
5-(2-oxo-1,2,3,4-tetrahydroquinolin-6-yl)-isobutyl-6-methyl-
5-(2-oxo-1,2,3,4-tetrahydroquinolin-6-yl)-3-sec.-butyl-6-methyl-
5-(2-oxo-1,2,3,4-tetrahydroquinolin-6-yl)-3-tert.-butyl-6-methyl-
5-(2-oxo-1,2,3,4-tetrahydroquinolin-6-yl)-6-methyl-3-pentyl-
5-(2-oxo-1,2,3,4-tetrahydroquinolin-6-yl)-3-allyl-6-methyl- and
5-(2-oxo-1,2,3,4-tetrahydroquinolin-6-yl)-6-methyl-3-propargyl-.

EXAMPLE 5

0.5 ml of triethylamine is added to a solution of 3 g of "B" in 30 ml of methylene chloride, and 0.8 ml of acetyl chloride is then added dropwise, with stirring. The mixture is stirred for a further hour at 20°, water is added and the mixture is worked up in the customary manner to give "C", melting point 207°.

The following 3,6-dihydro-1,3,4-thiadiazin-2-ones are obtained analogously:

5-(1-acetyl-1,2,3,4-tetrahydroquinolin-6-yl)-melting point 228°
5-(1-formyl-1,2,3,4-tetrahydroquinolin-6-yl)-6-methyl-
5-(1-propionyl-1,2,3,4-tetrahydroquinolin-6-yl)-6-methyl-, m.p. 198°
5-(1-butyryl-1,2,3,4-tetrahydroquinolin-6-yl)-6-methyl-
5-(1-isobutyryl-1,2,3,4-tetrahydroquinolin-6-yl)-6-methyl-
5-(1-valeryl-1,2,3,4-tetrahydroquinolin-6-yl)-6-methyl- 5-(1-isovaleryl-1,2,3,-tetrahydroquinolin-6-yl)-6-methyl- 5-(1-pivaloyl-1,2,3,4-tetrahydroquinolin-6-yl)-6-methyl-, melting point 173°

5-(1-benzoyl-1,2,3,4-tetrahydroquinolin-6-yl)-6-methyl-, m.p. 218°

5-(1-p-methoxy-benzoyl-1,2,3,4-tetrahydroquinolin-6-yl)-6-methyl-, melting point 233°

5-[1-(3,4-dimethoxy-benzoyl)-1,2,3,4-tetrahydroquinolin-6-yl]-6-methyl-, m.p. 127°

5-[1-(3,4-methylenedioxy-benzoyl)-1,2,3,4-tetrahydroquinolin-6-yl]-6-methyl-, m.p. 239°

5-(1-p-methylthio-benzoyl-1,2,3,4-tetrahydroquinolin-6-yl)-6-methyl- 5-(1-p-methylsulfinyl-benzoyl-1,2,3,4-tetrahydroquinolin-6-yl)-6-methyl- 5-(1-p-methylsulfonyl-benzoyl-1,2,3,4-tetrahydroquinolin-6-yl)-6-methyl- 5-(1-picolinoyl-1,2,3,4-tetrahydroquinolin-6-yl)-6-methyl- 5-(1-nicotinoyl-1,2,3,4-tetrahydroquinolin-6-yl)-6-methyl-, m.p. 159°

5-(1-isonicotinoyl-1,2,3,4-tetrahydroquinolin-6-yl)-6-methyl-, m.p. 228°

5-(1-methanesulfonyl-1,2,3,4-tetrahydroquinolin-6-yl)-6-methyl-, melting point 186°

5-(1-benzenesulfonyl-1,2,3,4-tetrahydroquinolin-6-yl)-6-methyl- 5-(1-p-toluenesulfonyl-1,2,3,4-tetrahydroquinolin-6-yl)-6-methyl- 5-(1-formyl-4,4-dimethyl-1,2,3,4-tetrahydroquinolin-6-yl)-6-methyl- 5-(1-acetyl-4,4-dimethyl-1,2,3,4-tetrahydroquinolin-6-yl)-6-methyl-, m.p. 199°

5-(1-propionyl-4,4-dimethyl-1,2,3,4-tetrahydroquinolin-6-yl)-6-methyl- 5-(1-butryl-4,4-dimethyl-1,2,3,4-tetrahydroquinolin-6-yl)-6-methyl- 5-(1-isobutyryl-4,4-dimethyl-1,2,3,4-tetrahydroquinolin-6-yl)-6-methyl-, m.p. 190°

5-(1-valeryl-4,4-dimethyl-1,2,3,4-tetrahydroquinolin-6-yl)-6-methyl- 5-(1-isovaleryl-4,4-dimethyl-1,2,3,4-tetrahydroquinolin-6-yl)-6-methyl- 5-(1-pivaloyl-4,4-dimethyl-1,2,3,4-tetrahydroquinolin-6-yl)-6-methyl- 5-(1-benzoyl-4,4-dimethyl-1,2,3,4-tetrahydroquinolin-6-yl)-6-methyl- 5-(1-p-methoxy-benzoyl-4,4-dimethyl-1,2,3,4-tetrahydroquinolin-6-yl)-6-methyl-, m.p. 131°

5-[1-(3,4-dimethoxy-benzoyl)-4,4-dimethyl-1,2,3,4-tetrahydroquinolin-6-yl]-6-methyl-, m.p. 134°

5-[1-(3,4-methylenedioxy-benzoyl)-4,4-dimethyl-1,2,3,4-tetrahydroquinolin-6-y]-6-methyl- 5-(1-p-methylthio-benzoyl)-4,4-dimethyl-1,2,3,4-tetrahydroquinolin-6-yl)-6-methyl- 5-(1-p-methylsulfinyl-benzoyl)-4,4-dimethyl-1,2,3,4-tetrahydroquinolin-6-yl)-6-methyl- 5-(1-p-methylsulfonyl-benzoyl)-4,4-dimethyl-1,2,3,4-tetrahydroquinolin-6-yl)-6-methyl- 5-(1-picolinoyl-4,4-dimethyl-1,2,3,4-tetrahydroquinolin-6-yl)-6-methyl- 5-(1-nicotinoyl-4,4-dimethyl-1,2,3,4-tetrahydroquinolin-6-yl)-6-methyl- 5-(1-isonicotinoyl-4,4-dimethyl-1,2,3,4-tetrahydroquinolin-6-yl)-6-methyl-, m.p. 148°

5-(1-methanesulfonyl-4,4-dimethyl-1,2,3,4-tetrahydroquinolin-6-yl)-6-methyl- 5-(1-benzenesulfonyl-4,4-dimethyl-1,2,3,4-tetrahydroquinolin-6-yl)-6-methyl-and 5-(1-p-toluenesulfonyl-4,4-dimethyl-1,2,3,4-tetrahydroquinolin-6-yl)-6-methyl-.

EXAMPLE 6

Analogously to Example 1, 5-(2-oxo-2,3,4,5-tetrahydro-1H-1-benazaepin-7-yl)-6-methyl-3,6-dihydro-1,3,4-thiadiazin-2-one ("D"), m.p. 230°, is obtained with 7-(2-chloropropionyl)-2,3,4,5-tetrahydro-1H-1-benzazepin-2-one (obtainable from 2,3,4,5-tetrahydro-1H-1-benzazepin-2-one and 2-chloropropionyl chloride according to Friedel-Crafts).

Analogously, the following 3,6-dihydro-1,3,4-thiadiazin-2ones are obtained:

5-(2-oxo-2,3,4,5-tetrahydro-1H-1-benzazepin-7-yl)-3,6-dimethyl- 5-(2-oxo-2,3,4,5-tetrahydro-1H-1-benzazepin-7-yl)-3-ethyl-6-methyl- 5-(1-methyl-2-oxo-2,3,4,5-tetrahydro-1H-1-benzazepin-7-yl)-

5-(1-methyl-2-oxo-2,3,4,5-tetrahydro-1H-1-benzazepin-7-yl)-6-methyl- 5-(1-methyl-2-oxo-2,3,4,5-tetrahydro-1H-1-benzazepin-7-yl)-3,6-dimethyl- 5-(2-oxo-5,5-dimethyl-2,3,4,5-tetrahydro-1H-1-benzazepin-7-yl)-

5-(2-oxo-5,5-dimethyl-2,3,4,5-tetrahydro-1H-1-benzazepin-7-yl)-6-methyl- 5-(2-oxo-5,5-dimethyl-2,3,4,5-tetrahydro-1H-1-benzazepin-7-yl)-3,6-dimethyl- 5-(1,5,5-trimethyl-2-oxo-2,3,4,5-tetrahydro-1H-1-benzazepin-7-yl)-

5-(1,5,5-trimethyl-2-oxo-2,3,4,5-tetrahydro-1H-1-benzazepin-7-yl)-6-methyl- 5-(1,5,5-trimethyl-2-oxo-2,3,4,5-tetrahydro-1H-1-benzazepin-7-yl)-3,6-dimethyl- 5-(1-ethyl-5,5-dimethyl-2-oxo-2,3,4,5-tetrahydro-1H-1-benzazepin-7-yl)-6-methyl- 5-(1-isopropyl-5,5-dimethyl-2-oxo-2,3,4,5-tetrahydro-1H-1-benzazepin-7-yl)-6-methyl- 5-(1-acetyl-2-oxo-2,3,4,5-tetrahydro-1H-1-benzazepin-7-yl)-

5-(1-acetyl-2-oxo-2,3,4,5-tetrahydro-1H-1-benzazepin-7-yl)-6-methyl- 5-(1-acetyl-2-oxo-2,3,4,5-tetrahydro-1H-1-benzazepin-7-yl)-3,6-dimethyl- 5-(1-acetyl-2-oxo-5,5-dimethyl-2,3,4,5-tetrahydro-1H-1-benzazepin-7-yl)-

5-(1-acetyl-2-oxo-5,5-dimethyl-2,3,4,5-tetrahydro-1H-1-benzazepin-7-yl)-6-methyl- 5-(1-acetyl-2-oxo-5,5-dimethyl-2,3,4,5-tetrahydro-1H-1-benzazepin-7-yl)-3,6-dimethyl-.

EXAMPLE 7

Analogously to Example 1, 5-(2,3,4,5-tetrahydro-1H-1-benzazepin-7-yl)-6-methyl-3,6-dihydro-1,3,4-thiadiazin-2-one ("E"), m.p. 142°, is obtained from 7-(2-chloropropionyl)-2,3,4,5-tetrahydro-1H-1-benzazepin [obtainable by reaction of 1-acetyl-2,3,4,5-tetrahydro-1H-1-benzazepine with 2-chloropropionyl chloride/AlCl3 to give 1-acetyl-2,3,4,5-tetrahydro-7-(2-chloropropionyl)-1H-1-benzazepine (in addition, the 8-(2-chloropropionyl) isomer is obtained, which can be separated chromatographically) and subsequent removal of the acetyl group with HCl].

In analogy, 5-(2,3,4,5-tetrahydro-1H-1-benzazepin-8yl)-6-methyl-3,6-dihydro-1,3,4-thiadiazin-2-one is obtained from 8-(2-chloropropionyl)-2,3,4,5-tetrahydro-1H-1-benzazepine.

EXAMPLE 8

In analogy to Example 1, 5-(1-methoxycarbonyl-2,3,4,5-tetrahydro-1H-1-benzazepin-7-yl)-6-methyl-3,6-dihydro-1,3,4-thiadiazin-2-one, m.p. 182°, is obtained from 1-methoxycarbonyl-2,3,4,5-tetrahydro-7-(2-chloropropionyl)-1H1-benzazepine (obtainable by reaction of 2,3,4,5-tetrahydro-1H-1-benzazepine with methyl chloroformate to give 1-methoxycarbonyl-2,3,4,5-tetrahydro-1H-1-benzazepine and subsequent reaction with 2-chloropropionly chloride/AlCl$_3$).

Analogously, there are obtained from the corresponding tetrahydro-1H-benzazepines:
5-(1-ethoxycarbonyl-2,3,4,5-tetrahydro-1H-1-benzazepin-7-yl)-6-methyl-3,6dihydro-1,3,4-thiadiazin-2-one, m.p. 162°
5-(1-acetyl-5,5-dimethyl-2,3,4,5-tetrahydro-1H-1-benzazepin-7-yl)-6-methyl-3,6-dihydro-1,3,4-thiadiazin-2-one.

EXAMPLE 9

Analogously to Example 4, 5-(2-oxo-2,3,4,5-tetrahydro-1H-1-benzazepin-7-yl)-3-ethyl-6-methyl-3,6-dihydro-1,3,4-thiadiazin-2-one is obtained from "D" and ethyl iodide.

Analogously, the following 3,5-dihydro-1,3,4-thiadiazin-2-ones are obtained by alkylation, alkenylation or alkynylation of the corresponding compounds of formula I (R$^1$=H):
5-(2-oxo-2,3,4,5-tetrahydro-1H-1-benzazepin-7-yl)-3-methyl
5-(2-oxo-2,3,4,5-tetrahydro-1H-1-benzazepin-7-yl)-3-ethyl
5-(2-oxo-2,3,4,5-tetrahydro-1H-1-benzazepin-7-yl)-3-butyl
5-(2-oxo-2,3,4,5-tetrahydro-1H-1-benzazepin-7-yl)-6-methyl-3-propyl
5-(2-oxo-2,3,4,5-tetrahydro-1H-1-benzazepin-b 7-yl)-3-isopropyl-6-methyl
5-(2-oxo-2,3,4,5-tetrahydro-1H-1benzazepin-7-yl)-3-butyl-6-methyl
5-(2-oxo-2,3,4,5-tetrahydro-1H-1-benzazepin-7-yl)-3-isobutyl-6-methyl
5-(2-oxo-2,3,4,5-tetrahydro-1H-1-benzazepin-7-yl)-3-sek.-butyl-6-methyl
5-(2-oxo-2,3,4,5-tetrahydro-1H-1benzazepin-7-yl)-3-tert.-butyl-6-methyl
5-(2-oxo-2,3,4,5-tetrahydro1H-1-benzazepin-7-yl)-6-methyl-3-pentyl
5-(2-oxo-2,3,4,5-tetrahydro-1H-1-benzazepin-7-yl)-3-allyl-6-methyl
5-(2-oxo-2,3,4,5-tetrahydro-1H-1-benzazepin-7-yl)-6-methyl-3-propargyl.

EXAMPLE 10

Analogously to Example 5, 5-[1-(3,4-dimethoxybenzoyl)-2,3,4,5-tetrahydro-1H-1-benzazepin-7-yl]-6-methyl-3,6-dihydro-1,3,4-thiadiazin-2-one, m.p. 207°, is obtained from "E".

Analogously, the following 3,6-dihydro-1,3,4-thiadiazin-2-ones are obtained.
5-(1-acetyl-2,3,4,5-tetrahydro-1H-1-benzazepin-7-yl)
5-(1-acetyl-2,3,4,5-tetrahydro-1H-1-benzazepin-7-yl)-6-methyl-, m.p. 184°
5-(1-formyl-2,3,4,5-tetrahydro-1H-1-benzazepin-7-yl)-6-methyl
5-(1-propionyl-2,3,4,5-tetrahydro-1H-1-benzazepin-7-yl)-6-methyl
5-(1-butyryl-2,3,4,5-tetrahydro-1H-1-benzazepin-7-yl)-6-methyl
5-(1-isobutyryl-2,3,4,5-tetrahydro-1H-1-benzazepin-7-yl)-6-methyl
5-(1-valeryl-2,3,4,5-tetrahydro-1H-1-benzazepin-7-yl)-6-methyl
5-(1-isovalery-2,3,4,5-tetrahydro-1H-1-benzazepin-7-yl)-6-methyl
5-(1-pivaloyl-2,3,4,5-tetrahydro-1H-1-benzazepin-7-yl)-6-methyl
5-(1-chloroacetyl-2,3,4,5-tetrahydro-1H-1-benzazepin-7-yl)-6-methyl-, oil
5-(1-glycyl-2,3,4,5-tetrahydro-1H-1-benzazepin-7-yl)-6-methyl
5-(1-N-methylaminoacetyl-2,3,4,5-tetrahydro-1H-1-benzazepin-7-yl)-6-methyl
5-(1-dimethylaminoacetyl-2,3,4,5-tetrahydro-1H-1-benzazepin-7-yl-6-methyl
5-(1-diethylaminoacetyl-2,3,4,5-tetrahydro-1H-1-benzazepin-7-yl)-6-methyl
5-(1-benzoyl-2,3,4,5-tetrahydro-1H-1-benzazepin-7-yl)-6-methyl
5-(1-p-methoxybenzoyl-2,3,4,5-tetrahydro-1H-1-benzazepin-7-yl)-6-methyl-, m.p. 231°
5-[1-(3,4-methylenedioxybenzoyl)-2,3,4,5-tetrahydro-1H-1-benzazepin-7-yl]-6-methyl
5-(1-p-methylthiobenzoyl-2,3,4,5-tetrahydro-1H-1-benzazepin-7-yl)-6-methyl
5-(1-p-methylsulfinylbenzoyl-2,3,4,5-tetrahydro-1H-1-benzazepin-7-yl)-6-methyl
5-(1-p-methylsulfonylbenzoyl-2,3,4,5-tetrahydro-1H-1-benzazepin-7-yl)-6-methyl
5-(1-p-fluorobenzoyl-2,3,4,5-tetrahydro-1H-1-benzazepin-7-yl)-6-methyl-, m.p. 237°
5-[1-(2-methoxy-4-methylthio-benzoyl)-2,3,4,5-tetrahydro-1H-1-benzazepin-7-yl]-6-methyl-, m.p. 209°
5-(1-cyclohexylcarbonyl-2,3,4,5-tetrahydro-1H-1-benzazepin7-yl)-6-methyl-, m.p. 146°
5-[1-(2-thenoyl)-2,3,4,5-tetrahydro-1H-1-benzazepin-7-yl]-6-methyl, m.p. 215°
5-[1-(3-thenoyl)-2,3,4,5-tetrahydro-1H-1-benzazepin-7-yl]-6-methyl
5-(1-picolinoyl-2,3,4,5-tetrahydro-1H-1-benzazepin-7-yl)-6-methyl
5-(1-nicotinoyl-2,3,4,5-tetrahydro-1H-1-benzazepin-7-yl)-6-methyl-, m.p. 230°
5-(1-isonicotinoyl-2,3,4,5-tetrahydro-1H-1-benzazepin-7-yl)-6-methyl-, m.p. 207°
5-(1-methanesulfonyl-2,3,4,5-tetrahydro-1H-1-benzazepin-7-yl)-6-methyl
5-(1-benzenesulfonyl-2,3,4,5-tetrahydro-1H-1-benzazepin-7-yl)-6-methyl
5-(1-p-toluenesulfonyl-2,3,4,5-tetrahydro-1H-1-benzazepin-7-yl)-6-methyl
5-(1-methoxycarbonyl-2,3,4,5-tetrahydro-1H-1-benzazepin-7-yl)-6-methyl-, m.p. 182°
5-(1-ethoxycarbonyl-2,3,4,5-tetrahydro-1H-1-benzazepin-7-yl)-6-methyl-, m.p. 162°
5-(1-propoxycarbonyl-2,3,4,5-tetrahydro-1H-1-benzazepin-7-yl)-6-methyl-,
5-(1-isopropoxycarbonyl-2,3,4,5-tetrahydro-1H-1-benzazepin-7-yl)-6-methyl-,
5-(1-butoxycarbonyl-2,3,4,5-tetrahydro-1H-1-benzazepin-7-yl)-6-methyl-,
5-(1-phenoxycarbonyl-2,3,4,5-tetrahydro-1H-1-benzazepin-7-yl)-6-methyl-, m.p. 234°

5-(1-aminocarbonyl-2,3,4,5-tetrahydro-1H-1-benzazepin-7-yl)-6-methyl-,
5-(1-N-methylaminocarbonyl-2,3,4,5-tetrahydro-1H-1-benzazepin-7-yl)-6-methyl-,
5-(1-N-ethylaminocarbonyl-2,3,4,5-tetrahydro-1H-1-benzazepin-7-yl)-6-methyl-,
5-(1-N,N-dimethylaminocarbonyl-2,3,4,5-tetrahydro-1H-1-benzazepin-7-yl)-6-methyl-,
5-(1-N,N-diethylaminocarbonyl-2,3,4,5-tetrahydro-1H-1-benzazepin-7-yl)-6-methyl,
5-(1-piperidonocarbonyl-2,3,4,5-tetrahydro-1H-1-benzazepin-7-yl)-6-methyl-,
5-(1-formylaminocarbonyl-2,3,4,5-tetrahydro-1H-1-benzazepin-7-yl)-6-methyl-,
5-(1-acetylaminocarbonyl-2,3,4,5-tetrahydro-1H-1-benzazepin-7-yl)-6-methyl-,
5-(1-propionylaminocarbonyl-2,3,4,5-tetrahydro-1H-1-benzazepin-7-yl)-6-methyl-,
5-(1-butyrylaminocarbonyl-2,3,4,5-tetrahydro-1H-1-benzazepin-7-yl)-6-methyl-,
5-(1-isobutyrylaminocarbonyl-2,3,4,5-tetrahydro-1H-1-benzazepin-7-yl)-6-methyl-,
5-[1-(3-methoxy-4-(2-hydroxyethoxy)-benzoyl)-2,3,4,5-tetrahydro-1H-1-benzazepin-7-yl]-6-methyl-, m.p. 221°
5-(1-methyl-1,2,3,4-tetrahydroquinolin-6-yl)-6-methyl-, m.p. 177°
5(1-isobutoxycarbonyl-1,2,3,4-tetrahydroquinolin-6-yl)-6-methyl-, m.p. 127°
5-[1-(2-methoxy-4-methylthio-benzoyl)-1,2,3,4-tetrahydroquinolin-6-yl]-6-methyl-, m.p. 160°
5[1-(2-methoxy-4-methylsulfinyl-benzoyl)-1,2,3,4-tetrahydroquinolin-6-yl]-6-methyl-, m.p. 138°
5(1-p-fluorobenzoyl-1,2,3,4-tetrahydroquinolin-6-yl)-6-methyl-, m.p. 221°
5-[1-(3-methoxy-4-methylsulfinyl-benzoyl)-1,2,3,4-tetrahydroquinolin-6-yl]-6-methyl-, m.p. 147°
5-(1-methoxycarbonyl-1,2,3,4-tetrahydroquinolin-6yl)-6-methyl-, m.p. 175°
5-[1-(3-phenyl-5-methyl-4-isoxazolyl-carbonyl)-1,2,3,4-tetrahydroquinolin-6-yl]-6-methyl-, m.p. 192°
5-[1-(2,4-dimethoxybenzoyl)-1,2,3,4-tetrahydroquinolin-6-yl]-6-methyl-, m.p. 162°
5-[1-(3,4,5-trimethoxybenzoyl)-1,2,3,4-tetrahydroquinolin-6-yl]-6-methyl-, m.p. 144°
5-(1-p-dimethylaminobenzoyl-1,2,3,4-tetrahydroquinolin-6-yl)-6-methyl-, m.p. 218°
5-[1-(3-methoxy-4-(2-methoxyethoxy)-benzoyl)-1,2,3,4-tetrahydroquinolin-6yl]-6-methyl-, m.p. ⅛°
5-(1-ethoxycarbonyl-1,2,3,4-tetrahydroquinolin-6-yl)-6-methyl-, m.p. 148°
5-[1-(3-methoxy-4-(2-hydroxyethoxy)-benzoyl)-1,2,3,4-tetrahydroquinolin-6-yl]-6-methyl-, m.p. 108°
5-(1-hydroxyacetyl-1,2,3,4,-tetrahydroquinolin-6-yl)-6-methyl-, m.p. 211°
5-[1-(3-methoxy-4-(3-dimethylaminopropoxy)-benzoyl)-1,2,3,4,-tetrahydroquinolin-6-yl]-6-methyl-, m.p. 151°
5-[1-(1,5,-dimethyl-3-pyrazolyl-carbonyl)-1,2,3,4,-tetrahydroquinolin-6yl]-6-methyl-, m.p. 223°
5-(1-methoxyacetyl-1,2,3,4-tetrahydroquinolin-6-yl)-6-methyl-, m.p. 156°
5-[1-(2-methyl-5-thiazolyl-carbonyl)-1,2,3,4-tetrahydroquinolin-6-yl]-6-methyl-, m.p. 221°
5-(1-dimethylaminoacetyl-1,2,3,4-tetrahydroquinolin-6-yl)-6-methyl-, m.p. 209°
5-[1-(1-imidazolycarbonyl)-1,2,3,4-tetrahydroquinolin-6-yl]-6-methyl-, m.p. 180°
5-(1-diethylaminoacetyl-1,2,3,4-tetrahydroquinolin-6-yl)-6-methyl-, m.p. 146°
5-(1-acetyl-1,2,3,4-tetrahydroquinolin-6-yl)-6-ethyl-, m.p. 168°
5-[1-(3,4-dimethoxybenzoyl)-1,2,3,4-tetrahydroquinolin-6-yl]-6-ethyl-, m.p. 253°
5-(1-isonicotinoyl-1,2,3,4-tetrahydroquinolin-6-yl)-6-ethyl-, m.p. 236°
5-(1-benzoyl-1,2,3,4-tetrahydroquinolin-6-yl)-6-ethyl-, m.p. 201°
5-(1-methoxycarbonyl-1,2,3,4-tetrahydroquinolin-6-yl)-6-ethyl-, m.p. 174°
5-(1-ethoxycarbonyl-1,2,3,4-tetrahydroquinolin-6-yl)-6-ethyl-, m.p. 158°
5-(1-hydroxyacetyl-1,2,3,4-tetrahydroquinolin-6-yl)-6-ethyl-, m.p. 228°
5-[1-(3-methoxy-4-(2-hydroxyethoxy)-benzoyl)-1,2,3,4-tetrahydroquinolin-6yl]-6-ethyl-, m.p. 171°
5-(1-acryloyl-4,4-dimethyl-1,2,3,4-tetrahydroquinolin-6-yl)-6-methyl-, m.p. 222°
5-(1-cyclopropylcarbonyl-4,4-dimethyl-1,2,3,4-tetrahydroquinolin-6-yl)-6-methyl-, m.p. 210°
5-(1-cyclohexylcarbonyl-4,4-dimethyl-1,2,3,4-tetrahydroquinolin-6-yl)-6-methyl-, m.p. 183°
5-(1-methoxyacetyl-4,4-dimethyl-1,2,3,4-tetrahydroquinolin-6-yl)-6-methyl-, m.p. 172°
5-(1-methoxycarbonyl-4,4-dimethyl-1,2,3,4-tetrahydroquinolin-6-yl)-6-methyl-, m.p. 212°
5-(1-ethoxycarbonyl-4,4-dimethyl-1,2,3,4-tetrahydroquinolin-6-yl)-6-methyl-, m.p. 182°
5-(1-N,N-diethylcarbamoyl-4,4-dimethyl-1,2,3,-tetrahydroquinolin-6-yl)-6-methyl-, m.p. 108°
5-[1-(1-methyl-4-poperidinyl-carbonyl)-4,4-dimethyl-1,2,3,4-tetrahydroquinolin-6-yl]-6-methyl-, m.p. 247°
5-(1-isobutyryl-4,4-dimethyl-1,2,3,4-tetrahydroquinolin-7-yl)-6-methyl-, m.p. 186°
5-(1-cyclopropylcarbonyl-4,4-dimethyl-1,2,3,4-tetrahydroquinolin-7-yl)-6-methyl-, m.p. 180°
5-(1-cyclohexycarbonyl-4,4-dimethyl-1,2,3,4-tetrahydroquinolin-7-yl)-6-methyl-,
5-(1-p-methoxybenzoyl-4,4-dimethyl-1,2,3,4-tetrahydroquinolin-7-yl)-6-methyl-, m.p. 193°
5-[1-(3,4-dimethoxybenzoyl)-4,4-dimethyl-1,2,3,4-tetrahydroquinolin-7-yl)-6-methyl-,
5-[1-(3-methoxy-4methylsulfinyl-benzoyl)-4,4-dimethyl-1,2,3,4-tetrahydroquinolin-7-yl)-6-methyl-, m.p. 134°
5-(1-isonicotinoyl-4,4-dimethyl-1,2,3,4-tetrahydroquinolin-7-yl)-6- methyl-, m.p. 152°
5-(1-methoxycarbonyl-4,4,-dimethyl-1,2,3,4-tetrahydroquinolin-7-yl)-6-methyl-, m.p. 194°
5-(1-ethoxycarbonyl-4,4-dimethyl-1,2,3,4-tetrahydroquinolin-7-yl)-6-methyl-, m.p. ¾°
5-(1-acetyl-4,4,-diethyl-1,2,3,4-tetrahydroquinolin-6-yl)-6-methyl-, m.p. 210°
5-(1-isonicotinoyl-4,4-diethyl-1,2,3,4-tetrahydroquinolin-6-yl)-6-methyl-, m.p. 183°

EXAMPLE 11

Analogously to Example 2, the following 3,6-dihydro-1,3,4-thiadiazin-2-ones are obtained from the corresponding (2-chloropropionyl)-1,2,3,4-tetrahydroquinolines:

5(4,4-dimethyl-1,2,3,4-tetrahydroquinolin-6-yl)-6-methyl-, m.p. 201°
5-(4,4,-dimethyl-1,2,3,4-tetrahydroquinolin-7-yl)-6-methyl-, m.p. 187°

The following examples relate to pharmaceutical formulations containing compounds of the formula I or their acid addition salts:

Example A: Tablets

A mixture of 1 kg of "A", 10 kg of Lactose, 6 kg of microcrystalline cellulose, 6 kg of potato starch, 1 kg of polyvinylpyrrolidone, 0.8 kg of talc and 0.1 kg of magnesium stearate is pressed to tablets in the customary manner such that each tablet contains 10 mg of active compound.

Example B: Coated tablets

Tablets are pressed analogously to Example A and are subsequently coated in the customary manner with a coating of sucrose, potato starch, talc, tragacanth and coloring substance.

Example C: Capsules

Hard gelatin capsules are filled with 1 kg of 5-(2-oxo-4,4,-dimethyl-1,2,3,4-tetrahydroquinolin-6-yl)-6-methyl-3,6dihydro-1,3,4-thiadiazin-2-one in the customary manner such that each capsule contains 5 mg of active compound.

Example D: Ampoules

A solution of 1 kg of "C" in 30 l of 1,2-propanediol is subjected to sterile filtration, and ampoules are filled with the solution, lyophilized under sterile conditions and subjected to sterile sealing. Each ampoule contains 2 mg of active compound.

Tablets, coated tablets, capsules and ampoules which contain one or more of the other active compounds of the formula I and/or their physiologically acceptable acid addition salts can be obtained analogously.

The preceding examples can be repeated with similar success by substituting the generically or specifically described reactants and/or operating conditions of this invention for those used in the preceding examples.

From the foregoing description, one skilled in the art can be easily ascertain the essential characteristics of this invention, and without departing from the spirit and scope thereof, can make various changes and modifications of the invention to adapt it to various usages and conditions.

What is claimed is:

1. A thiadiazinone of the formula

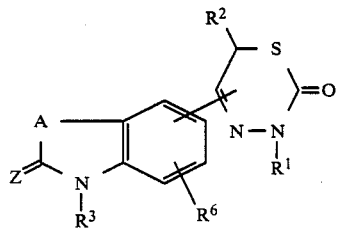

wherein

A is —$CHR^4$—$CHR^5$, —$CH_2$—$CR^4R^5$—, —$CR^1$—$R^5$—$CH^2$—, —$CHR^4$—$CHR^5$—$CH_2$—, —$CH^4$—$CH_2$—$CHR^5$—, —$CH_2$—$CHR^4$—$CHR^5$—, —$CR^4R^5$—$CH_2CH_2$—, —$CH_2$—$CR^4R^5$—$CH_2$— or —$CH_2CH_2$—$CR^4R^5$, $R^1$, $R^2$, $R^3$, $R^4$ and $R^5$ are each independently H, $C_{1-5}$-alkyl, $C_{2-5}$-alkenyl or $C_{2-5}$-alkinyl, or $R^3$ is alkanoyl, alkenoyl or alkinoyl with up to 10 C atoms each; hydroxyacetyl; methoxyacetyl; chloroacetyl; aminoacetyl; N-methylaminoacetyl; N,N-diethylaminoacetyl; aroyl with 7–15 C atoms, optionally substituted by 1–3 of $C_{1-3}$-alkyl, $C_{1-3}$-alkoxy, $C_{1-3}$alkylthio, $C_{1-3}$alkylsulfinyl, $C_{1-3}$-alkylsulfonyl, methylenedioxy, OH, F, Cl, Br, I, $NO_2$, $NH_2$, $C_{1-3}$-alkylamino, or di($C_{1-3}$-alkyl)-amino; 2- or 3-methoxy-4-(2-hydroxyethoxy)-benzoyl; 2- or 3-methoxy-4-(2methoxyethoxy)-benzoyl; $C_{6-10}$-aryl-$C_{1-4}$-alkanoyl; o—, m— or p-methoxyphenylacetyl; $C_{3-8}$-cycloalkylcarbonyl; $C_{1-8}$-alkylsulfonyl; $C_{6-15}$-arylsulfonyl; o—, m— or p-methoxybenzenesulfonyl; $C_{1-8}$-alkoxycarbonyl; fluorinated $C_{1-8}$-alkoxycarbonyl; $C_{3-8}$cycloalkoxycarbonyl; $C_{6-10}$-aryloxycarbonyl; o—, m— or p-methoxyphenoxycarbonyl; aminocarbonyl; N-$C_{1-8}$-alkylaminocarbonyl; N,N-di-($C_{1-8}$-alkyl)aminocarbonyl; dialkylaminoalkanoyl with 4–14 carbon atoms; dialkylaminocarbonyl with 3–9 carbon atoms; N-$C_{3-8}$-cycloalkylaminocarbonyl; N,N-Di-($C_{3-8}$-cycloalkyl)-aminocarbonyl; N-$C_{6-10}$-arylaminocarbonyl; $C_{1-8}$-alkanoylaminocarbonyl, methoxymethylthiobenzoyl; 2- or 3-thenoyl; is H, $C_{1-5}$-alkyl, $C_{2-5}$-alkoxy, OH, F, Cl, Br or I and is 2 hydrogen atoms, H and $C_{1-5}$-alkyl, or 2 independent $C_{1-5}$-alkyl groups, or a salt thereof.

2. A thiadiazinone according to claim 1, wherein $R^1$, $R^2$, $R^4$ and $R^5$ are independently methyl, ethyl, propyl, allyl, vinyl, propen-1-yl, propargyl, ethinyl or propin-1-yl.

3. A thiadiazinone of the formula

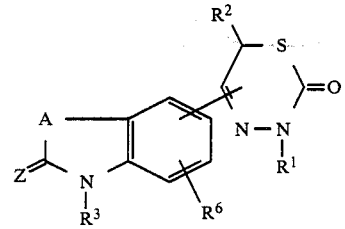

wherein $R^3$ is methyl, ethyl, propyl, allyl, vinyl, propen-1-yl, propargyl, ethinyl, propin-1-yl, acetyl, formyl, propionyl, butyryl, isobutyryl, valeryl, isovaleryl or pivaloyl (trimethylacetyl), acryloyl, hydroxyacetyl, methoxyacetyl, chloroacetyl, aminoacety(glycyl), N-methylaminoacetyl, N,N-dimethylaminoacetyl, N,N-diethylaminoacetyl, pyrrolidinoacetyl, piperidinoacetyl; benzoyl; o—, m— or p-toluyl; o—, m— or p-methoxybenzoyl; 2,3-, 2,4-, 2,5-, 2,6-, 3,4- or 3,5-dimethoxybenzoyl; 2,3,4-, 2,3,5-, 2,3,6-, 2,4,5-, 2,4,6- or 3,4,5-trimethoxybenzoyl; o—, m— or p-methylthiobenzoyl; o—, m— or p-methylsulfinylbenzoyl; o—, m— or p-methylsulfonyl-benzoyl; 2,3- or 3,4-methylenedioxybenzoyl; o—, m— or p-fluorobenzoyl; o—, m— or p-chlorobenzoyl; 2- or 3-methoxy-4-methylthiobenzoyl; 2- or 3-methoxy-4-methylsulfinylbenzoyl; o—, m— or p-dimethylaminobenzoyl; 2- or 3-methoxy-4-(2-hydroxyethoxy-benzoyl; 2- or 3-methoxy-4-(2-methoxyethoxy)-benzoyl; 1- or 2-naphthoyl; 2- or 3-furoyl; 2- or 3-thenoyl; isoxazoyl-4-carbonyl; 3-phenyl-5-methyl-isoxazolyl-4-carbonyl; 1,5-dimethyl-pyrazolyl-3-carbonyl; 2-methyl-thiazolyl-4- or -5-carbonyl; 1-imidazolyl-carbony6; picolinoyl; nicotinoyl; isonicotinoyl; 1-methyl-2-, -3- or -4- piperidinyl-carbonyl; phenylacetyl; o— m— or p-methoxyphenylacetyl; 2- or 3-phenylpropionyl; 2-, 3- or 4-phenylbutyryl; cyclopropylcarbonyl; cyyclopentylcarbonyl; cyclohexylcarbonyl; nethyl-, ethyl-, propyl- or butylsulfonyl; benzenesulfonyl; o—, m— or p-toluenesulfonyl; o—, m— or p-methoxybenzenesulfonyl; 1- or 2-naphthalenesulfonyl; methoxycarbonyl; ethoxycarbonyl; propoxycarbonyl; isopropoxycarbonyl; butoxycarbonyl; isobutoxycarbonyl, 2,2,2-trifluoroethoxycarbonyl; cyclopropoxycarbonyl; cyclobutoxycarbonyl; cyclopentoxycarbonyl; cyclohexoxycarbonyl; phenoxycarbonyl, o—, m— or p-methoxyphenoxycarbonyl; aminocarbonyl; N-methyl- or N-ethylaminocarbonyl; N,N-dimethyl- or N,N-diethylaminocarbonyl; N-cyclopropylaminocarbonyl; N-cyclobutylamino-carbonyl; N-cyclopentylaminocarbonyl, N-cyclohexylaminocarbonyl; N,N-dicyclopropylaminocarbonyl; pyrrolidinocarbonyl; piperidioncarbonyl; anilinocarbonyl; formylaminocarbonyl; acetylaminocarbonyl; propionylaminocarbonyl; butyrylaminocarbonyl; or isobutyrylaminocarbonyl, A is —CHR$^4$—CHR$^5$, —CH$_2$—CR$^4$R$^5$—, —CR$^4$R$^5$—CH$_2$—, —CHR$^4$—CHR$^5$—CH$_2$—, —CH$^4$—CH$_2$—CHR$^5$—, —CH$_2$—CHR$^4$—CHR$^5$—, —CR$^4$R$^5$—CH$_2$CH$_2$—, —CH$_2$—CR$^4$R$^5$—CH$_2$— or —CH$_2$CH$_2$—CR$^4$R$^5$, R$^1$, R$^2$, R$^4$ and R$^5$ are each independently H, C$_{1-5}$-alkyl, C$_{2-5}$-alkenyl or C$_{2-5}$-alkinyl, R$^6$ is H, C$_{1-5}$-alkyl, C$_{2-5}$-alkoxy, OH, F, Cl, Br or I and Z is 2 hydrogen atoms, H and C$_{1-5}$-alkyl, or 2 independent C$_{1-5}$-alkyl groups.

4. A thiadiazinone according to claim 1, wherein R$^6$ is methoxy, ethoxy or propoxy.

5. A thiadiazinone according to claim 1, wherein the dihydrothiadiazinone ring is in the 6- or the 7-position of a tetrahydroquinoline ring or in the 8-position of a tetrahydrobenzazepine ring.

6. A tetrahydroquinolinyl-1,3,4-thiadiazin-2-one according to claim 1, wherein A is —CHR$^4$—CHR$^5$—, —CH$_2$— CR$^4$CR$^5$— or —CR$^4$R$^5$—CH$_2$—.

7. A tetrahydrobenzazepinyl-1,3,4-thiadiazin-2-one according to claim 1, wherein A is —CHR$^4$—CHR$^5$—CH$_2$—, —CHR$^4$—CH$_2$—CHR$^5$—, —CH$_2$—CHR$^4$—CHR$^5$—, —CR$^4$R$^5$—CH$_2$CH$_2$—, —CH$_2$—CR$^4$R$^5$—CH$_2$— or —CH$_2$CH$_2$—CR$^4$R$^5$—.

8. A tetrahydroquinolinyl-1,3,4-thiadiazin-2-one according to claim 6, wherein the dihydrothiadiazinone ring is in the 6- or 7-position,
R$^1$ is H or C$_{1-5}$-alkyl,
R$^2$, R$^4$ and R$^5$ are each independently H or methyl,
R$^6$ is H and
Z is 2 hydrogen atoms.

9. A tetrahydroquinolinyl-1,3,4-thiaziazin-2-one-one according to claim 6, wherein the dihydrothiadiazinone ring is in the 6- or 7-position,
R$^1$ is H or alkyl with 1-3 C atoms,
R$^2$, R$^4$ and R$^5$ are each independently H or methyl,
R$^3$ is C$_{1-6}$-alkanoyl, benzoyl, toluyl, methoxybenzoyl, dimethioxybenzoyl, methylthiobenzoyl, methylsulfinyl-benzoyl, C$_{1-6}$-alkylsulfonyl, benzenesulfonyl or toluenesulfonyl,
R$^6$ is H and
Z is 2 hydrogen atoms.

10. A tetrahydroquinolinyl-1,3,4-thiadiazin-2-one-one according to claim 6, wherein the dihydrothiadiazinone ring is in the 6- or 7-position.
R$^1$ is H or C$_{1-3}$-alkyl,
R$^2$, R$^4$ and R$^5$ are each independently H or methyl,
R$^3$ is C$_{1-5}$-alkanoyl,
R$^6$ is H and
Z is 2 hydrogen atoms.

11. A tetrahydrobenzazepinyl-1,3,4-thiadiazin-2-one according to claim 7, wherein the dihydrothiadiazoinone ring is in the 7-position or 8-position,
R$^1$ is H, or C$_{1-3}$-alkyl,
R$^2$, R$^3$, R$^4$ and R$^5$ are each independently H or methyl,
R$^6$ is H and
Z is 2 hydrogen atoms.

12. A tetrahydrobenzazepinyl-1,3,4-thiadiazin-2-one according to claim 7, wherein the dihydrothiadiazinone ring is in the 7-position or 8-position,
R$^1$ is H, or C$_{1-3}$-alkyl,
R$^2$, R$^4$ and R$^5$ are each independently H or methyl,
R$^3$ is C$_{1-3}$-alkanoyl, cyclohexylcarbonyl, benzoyl, toluyl, methoxybenzoyl, dimethoxybenzoyl, methylthio-benzoyl, methylsulfinyl-benzoyl, methylsulfonylbenzoyl, fluorobenzoyl, methoxymethylthiobenzoyl, 2- or 3-thenoyl, C$_{1-6}$-alkylsulfonyl, benzene sulfonyl, toluene sulfonyl, C$_{2-6}$-alkoxycarbonyl, phenoxycarbonyl, C$_{2-6}$-alkylaminocarbonyl, or C$_{2-6}$-alkanoylaminocarbonyl,
R$^6$ is H and
Z is 2 hydrogen atoms.

13. A tetrahydrobenzazepinyl-1,3,4-thiadiazin-2-one according to claim 3, wherein the dihydrothiadiazinone ring is in the 7-position or 8-position,
R$^1$, R$^4$, R$^5$ and R$^6$ are each H,
R$^2$ is methyl,
R$^3$ is cyclohexylcarbonyl, methoxybenzoyl, dimethoxybenzoyl, fluorobenzoyl, 2-methoxy-4methylthiobenzoyl, methoxycarbonyl, ethoxycarbonyl or phenoxycarbonyl and
Z is 2 hydrogen atoms.

14. 5-[1-(3,4-Dimethoxybenzoyl)-1,2,3,4-tetrahydroquinolin-6-yl]-6-methyl-3,6-dihydro-1,3,4-thiadiazin-2-one.

15. 5-(1-Isonicotinoyl-4,4-diethyl-1,2,3,4-tetrahydroquinolin-6-yl)-6-methyl-3,6-dihydro-1,3,4-thiadiazin-2-one.

16. A pharmaceutical composition comprising an effective amount of a compound of claim 1 and a pharmaceutically acceptable carrier.

17. A method of treating cardiac insufficiency in a patient in need of such treatment comprising administering an effective amount of a compound of claim 1.

18. A method according to claim 17, wherein the effective amount is 0.02–2 mg/kg of body weight of the patient.

* * * * *

UNITED STATES PATENT AND TRADEMARK OFFICE
CERTIFICATE OF CORRECTION

PATENT NO. : 4,916,128

DATED : April 10, 1990

INVENTOR(S) : ROCHUS JONAS ET AL

It is certified that error appears in the above-identified patent and that said Letters Patent is hereby corrected as shown below:

Column 17, claim 1, line 60:

reads "A is $-CHR^4-CHR^5$, $-CH_2-CR^4R^5-$, $-CR^{1-}$"

should read -- A is $-CHR^4-CHR^5$, $-CH_2-CR^4R^5-$, $-CR^{4-}$ --

Column 17, claim 1, line 61:

reads "$R^5-CH^2-$, $-CHR^4-CHR^5-CH_2-$, $-CH-$"

should read -- $R^5-CH_2-$, $-CHR^4-CHR^5-CH_2-$, $-CH-$ --

Column 18, claim 1, line 22:

reads "methoxymethylthiobenzoyl; 2- or 3-thenoyl; is H,"

should read -- methoxymethylthiobenzoyl; 2- or 3-thenoyl; --

Column 18, claim 1, line 23:

reads "$C_{1-5}$-alkyl, $C_{2-5}$-alkoxy, OH, F, CL, Br or I and is 2"

should read --$R^6$ is H, $C_{1-5}$-alkyl, $C_{2-5}$-alkoxy, OH, F, Cl, Br or I and --

UNITED STATES PATENT AND TRADEMARK OFFICE
CERTIFICATE OF CORRECTION

PATENT NO. : 4,916,128

DATED : April 10, 1990

INVENTOR(S) : ROCHUS JONAS ET AL

It is certified that error appears in the above-identified patent and that said Letters Patent is hereby corrected as shown below:

Column 18, claim 1, line 24:

reads "hydrogen atoms, H and $C_{1-5}$-alkyl, or 2 indepen-"

should read -- Z is 2 hydrogen atoms, H and $C_{1-5}$-alkyl, or 2 indepen- --

Signed and Sealed this

Eighteenth Day of September, 1990

Attest:

HARRY F. MANBECK, JR.

*Attesting Officer*  *Commissioner of Patents and Trademarks*